United States Patent
Yoon et al.

(10) Patent No.: US 11,684,650 B2
(45) Date of Patent: Jun. 27, 2023

(54) COMPOSITION FOR PREVENTING, ALLEVIATING, OR TREATING CACHEXIA AND MUSCLE LOSS

(71) Applicant: CHUNG-ANG UNIVERSITY INDUSTRY ACADEMIC COOPERATION FOUNDATION, Seoul (KR)

(72) Inventors: Yoo Sik Yoon, Seoul (KR); Jae Woong Jang, Anyang-si (KR); Se Yeon Chae, Seongnam-si (KR); Tae Hyun Bae, Ansan-si (KR); Hyun Ji Lee, Seoul (KR); Jae Won Song, Gwangmyeong-si (KR)

(73) Assignee: CHUNG-ANG UNIVERSITY INDUSTRY ACADEMIC COOPERATION FOUNDATION, Seoul (KR)

(*) Notice: Subject to any disclaimer, the term of this patent is extended or adjusted under 35 U.S.C. 154(b) by 163 days.

(21) Appl. No.: 15/733,566

(22) PCT Filed: Feb. 28, 2019

(86) PCT No.: PCT/KR2019/002446
§ 371 (c)(1),
(2) Date: Nov. 5, 2020

(87) PCT Pub. No.: WO2019/168388
PCT Pub. Date: Sep. 6, 2019

(65) Prior Publication Data
US 2021/0052688 A1 Feb. 25, 2021

(30) Foreign Application Priority Data
Feb. 28, 2018 (KR) .................. 10-2018-0024847

(51) Int. Cl.
*A61K 36/00* (2006.01)
*A61K 36/65* (2006.01)
*A61P 21/06* (2006.01)

(52) U.S. Cl.
CPC .............. *A61K 36/65* (2013.01); *A61P 21/06* (2018.01); *A61K 2236/333* (2013.01)

(58) Field of Classification Search
CPC ...................................................... A61P 35/00
See application file for complete search history.

(56) References Cited

U.S. PATENT DOCUMENTS 4,613,591 A 9/1986 Aburada et al.

FOREIGN PATENT DOCUMENTS

| EP | 1401458 B1 | 1/2011 |
| JP | 2008-519767 | 6/2008 |
| JP | 2009-046391 | 3/2009 |
| JP | 2012-121846 | 6/2012 |
| KR | 10-1332836 | 11/2013 |
| KR | 10-1693828 | 1/2017 |

OTHER PUBLICATIONS

Choi et al, Effect of Sipjeondaebo-Tang on Cancer-Induced Anorexia and Cachexia in CT-26 Tumor-Bearing Mice. Mediators of Inflammation, (2014) vol. 2014, pp. Article (Year: 2014).*
Kang et al., Yield of Paeonia Radix and changes of paeoniflorin concentration in Paeonia Radix with different growing stages. Korean Journal of Crop Science (1994), vol. 39, No. 4, pp. 397-404 (Year: 1994).*
Ou, Paeonia lactiflora Pall inhibits bladder cancer growth involving phosphorylation of Chk2 in vitro and in vivo. Journal of ethnopharmacology, (Apr. 26, 2011) vol. 135, No. 1, pp. 162-172 (Year: 2011).*
Choi et al. "Effect of Sipjeondaebo-Tang on Cancer-Induced Anorexia and Cachexia in CT-26 Tumor-Bearing Mice" Mediators of inflammation, 2014: 736563 (2014) (10 pages).
International Search Report corresponding to PCT/KR2019/002446; dated Jun. 9, 2019 (5 pages, including English translation).
Woo et al. "Sip-jeon-dea-bo-tang, a traditional herbal medicine, ameliorates cisplatin-induced anorexia via the activation of JAK1/STAT3-mediated leptin and IL-6 production in the fat tissue of mice" Molecular Medicine Reports, 13(4): 2967-2972 (2016).
Chinese Office Action and English translation corresponding to Chinese Patent Application No. 201980028639.1 dated Oct. 19, 2021 (23 pages).
Cong Ming-Hua et al. "Mechanisms of Anorexia Cancer Cachexia Syndrome and Potential Benefits of Traditional Medicine and Natural Herbs" Current Pharmaceutical Biotechnology 17(13):1147-1152 (2016).
Database WPI. Week 200921, Thomson Scientific, London GB; AN 2009-E71964, XP002804811, CN 101347518 Tianjin Tasly Pharm Co Ltd (Jan. 21, 2009) (Abstract only).
Database WPI. Week 201415, Thomson Scientific, London GB; AN 2013-V84262, XP002804810, CN 103301282; Univ Chengdu TCM (Sep. 18, 2013) (Abstract only).
Extended European Search Report corresponding to EP 19761453.0; dated Dec. 13, 2021 (9 pages).

(Continued)

*Primary Examiner* — Qiuwen Mi
(74) *Attorney, Agent, or Firm* — Myers Bigel, P.A.

(57) ABSTRACT

The present disclosure relates to a composition containing a Paeoniae radix extract as an active ingredient. The composition may alleviate inappetence, weight loss, muscle loss and fatigue and inhibit hematopoietic toxicity. Thus, the composition may be effectively used for the prevention, alleviation or treatment of cachexia and muscle loss.

6 Claims, 9 Drawing Sheets

(56) References Cited

OTHER PUBLICATIONS

Xu Shucai. "Clinical Observation of Peony Liquorice Decoction in Treating Patients with Advanced Cancer" Journal of Liaoning University of TCM, 18(6):183-185 (Jun. 2016) (English Abstract only).
Gao, Guang-Hui, et al., "HPLC Determination of Peoniflorin in Traditional Chinese Medicine and Health Food with Solid Phase Extraction", PTCA (Part B: Chem. Anal.), 51 (with English abstract), 2015, 228-230.

* cited by examiner

COMPOSITION FOR PREVENTING, ALLEVIATING, OR TREATING CACHEXIA AND MUSCLE LOSS

CROSS REFERENCE TO RELATED APPLICATIONS

This application is a 35 U.S.C. § 371 national stage application of PCT International Application No. PCT/KR2019/002446, filed Feb. 28, 2019, which claims priority from Korean Patent Application No. 10-2018-0024847, filed Feb. 28, 2018, the contents of which are incorporated herein in their entireties by reference. The above-referenced PCT International Application was published in the Korean language as International Publication No. WO 2019/168388 A1 on Sep. 6, 2019.

TECHNICAL FIELD

The present disclosure relates to a composition for preventing, alleviating, or treating cachexia containing a Paeoniae radix extract as an active ingredient.

BACKGROUND ART

Cachexia is a syndrome that is commonly associated with chronic diseases such as cancer, tuberculosis, AIDS, and chronic obstructive pulmonary disease, and refers to a catabolic state of body metabolism characterized by persistent inappetence and weight loss, resulting in malnutrition, metabolic imbalance, and loss of muscle or fat. Cancer patients suffers from not only cachexia but also side effects of various anticancer therapies, unlike patients of other chronic diseases (Fearon K. et al., Lancet Oncol 2011; 12(5):489-495).

Cachexia occurs in 50 to 80% of the patients of gastrointestinal and lung cancer, and the mortality caused by cachexia reaches 20 to 30%. Cancer cachexia is characterized by weight loss due to the loss of muscle resulting from inflammatory responses caused by various cytokines and the increases in catabolism caused by metabolic changes. These changes lower the response rate to chemotherapy or radiotherapy making effective therapy difficult, and also lower the quality of life of the patients.

Mechanism of cachexia includes the change in the activity of the neuroendocrine system, secretion of various inflammatory cytokines (IL-1-beta, IL-6, and TNF-α) and cancer-specific cachectic factors, resulting in a decrease in food intake and metabolic changes. Among them, inflammatory cytokines, which are proteins secreted directly from tumors or produced by immune cells in response to tumors playing an important role in controlling immune system, are a major cause of cachexia by inducing inappetence and weight loss (Argiles J M et al., Curr. Opin. Clin. Nutr. Metab. Care 1998; 1:245-251). Inflammatory cytokines are known to induce inappetence by causing changes in taste or gastrointestinal function (Durham W J et al., Curr Opin Clin Nutr Metab Care. 2009; 12:72-77).

Muscle loss is one of the most important features of cachexia, and is known to be caused by an increase in protein catabolism and a decrease in protein anabolism due to over-activation of various inflammatory cytokines. Symptoms of cachexia significantly overlap with symptoms of muscle loss. Almost all patients with cachexia have muscle loss, but only a portion of patients with muscle loss show cachexia symptoms. In a clinical point of view, muscle loss can be considered as a sign of cachexia. Inflammatory cytokines that contribute to cachexia affect insulin and testosterone, which are major factors regulating muscle metabolism, and cause abnormalities in muscle protein synthesis (Seungwan Ryu, J. Clin. Nutr. 2017; 9:2-6).

Currently, a progesterone formulation (megestrol acetate; megace) and steroids (dexamethasone, and prednisone), etc. are used for the treatment of cachexia. However, the steroids have no long-lasting therapeutic effect, and show side effects such as water retention, insulin resistance, and adrenal gland hypofunction, when used for a long period of time, and thus only short-term prescriptions of the steroids are permitted. The progesterone formulation (megace) was approved for use in AIDS patients showing anorexia or weight loss by the US FDA, and is currently approved for the treatment of cancer cachexia in Korea. Thus, the progesterone formulation was used as a comparative drug in the present disclosure. However, the progesterone formulation increases adipose tissue rather than muscle, and has side effects such as thromboembolism, edema, hyperglycemia, erectile dysfunction, uterine bleeding, and adrenal gland hypofunction.

Patients with cachexia show a low response to anticancer therapy and experience serious side effects. Anticancer treatments for cancer patients broadly include surgical operation, chemotherapy, and radiotherapy. Surgical operation is a treatment method for removing a lesion (i.e., cancer). Early-stage cancer can be completely cured only by surgical operation, but middle or later stage cancer cannot be cured by only surgical operation. Chemotherapy, radiotherapy, or combination therapy thereof is commonly used to remove cancer cells by generating free radicals, but these therapies have low specificity, and thus also damage normal cells having characteristics of dividing and proliferating rapidly, such as hematopoietic cells or immune cells. Therefore, these therapies cause side effects such as vomiting, inappetence, stomatitis, diarrhea, constipation, fever, infection, leukopenia, thrombocytopenia, anemia, abdominal pain, nephrotoxicity, hapatotoxicity, cardiotoxicity, peripheral neurotoxicity, central nervous system toxicity, muscle pain, bone pain, bone marrow suppression, and the like. Cachexia and muscle loss, which occur at a high frequency in cancer patients, lower the response rate to anticancer therapy, make it difficult to achieve effective anticancer therapy, and lower the quality of life of the patients.

Therefore, in order to treat cachexia and muscle loss occurring in cancer and other diseases, there is a need to develop a safe and effective therapy that are superior to existing therapeutic agents.

DISCLOSURE

Technical Problem

An object of the present disclosure is to provide a pharmaceutical composition for preventing or treating cachexia and muscle loss, the pharmaceutical composition containing a Paeoniae radix extract as an active ingredient.

Another object of the present disclosure is to provide a food composition for preventing or alleviating cachexia and muscle loss, the food composition containing a Paeoniae radix extract as an active ingredient.

Still another object of the present disclosure is to provide an anticancer adjuvant containing a pharmaceutical composition for preventing or treating cachexia and muscle loss, the pharmaceutical composition containing a Paeoniae radix extract as an active ingredient.

Technical Solution

One aspect of the present disclosure provides a pharmaceutical composition for preventing or treating cachexia and muscle loss, the pharmaceutical composition containing a Paeoniae radix extract as an active ingredient.

According to one embodiment of the present disclosure, the Paeoniae radix extract may be obtained by extraction with a solvent selected from the group consisting of distilled water, a $C_1$ to $C_4$ lower alcohol, hexane, ethyl acetate, chloroform, diethyl ether, dichloromethane, acetone, and mixtures thereof.

According to another embodiment of the present disclosure, the cachexia may be caused by cancer.

According to still another embodiment of the present disclosure, the cachexia may be caused by anticancer drug.

According to yet another embodiment of the present disclosure, the composition may alleviate a symptom selected from the group consisting of inappetence, weight loss, fatigue, inflammation, muscle loss, and hematopoietic toxicity.

Another aspect of the present disclosure provides a food composition for preventing or alleviating cachexia and muscle loss, the food composition containing a Paeoniae radix extract as an active ingredient.

Still another aspect of the present disclosure provides an anticancer adjuvant containing, as an active ingredient, a pharmaceutical composition for preventing or treating cachexia and muscle loss, the pharmaceutical composition containing a Paeoniae radix extract as an active ingredient.

Advantageous Effects

The composition containing a Paeoniae radix extract as an active ingredient may alleviate inappetence, weight loss, muscle loss and fatigue and inhibit hematopoietic toxicity. Thus, the composition may be effectively used for the prevention, alleviation or treatment of cachexia and muscle loss.

BRIEF DESCRIPTION OF DRAWINGS

FIG. 6 shows the results of measuring food intake (A) and body weight (B) depending on dose after administering a Paeoniae radix extract at a dose of 50, 100 or 200 mg/kg to mice with tumors induced by LLC cells.

BEST MODE

To achieve the above-described objects, one aspect of the present disclosure provides a pharmaceutical composition for preventing or treating cachexia and muscle loss, the pharmaceutical composition containing a Paeoniae radix extract as an active ingredient.

As used herein, the term "cachexia" refers to a high degree of general weakness that can be seen at the end stage of cancer, tuberculosis, diabetes, acquired immunodeficiency syndrome (AIDS), and the like. Cachexia is frequently seen in patients with gastrointestinal cancer such as gastric cancer, esophageal cancer, and colorectal cancer, and in patients with lung cancer. Patients with cachexia shows symptoms such as inappetence, loss of weight and stamina, anemia, lethargy, and indigestion. In particular, patient with cachexia have difficulty of food intake due to inappetence, or losing weight even though normal intake of food. Cancer patient with cachexia show a low response to anticancer chemotherapy or radiotherapy. Cachexia reduces the quality of life of the patients, shortens life expectancy, and causes death due to weight loss in 10 to 20% of all cancer patients.

As used herein, the term "muscle loss" refers to a condition in which muscles in the body are decreased. For example, the muscle loss may be a decrease in muscle tissue caused by not using muscle, a decrease in muscle tissue caused by a disease of the muscle itself, or a decrease in muscle tissue caused by damage to a nerve that controls the muscle. This muscle loss may be caused by, for example, cachexia.

According to one embodiment of the present disclosure, the cachexia may be caused by cancer. Specifically, the cachexia may be caused by an anticancer drug used for cancer treatment. The anticancer drug may be selected from the group consisting of doxorubicin, irinotecan, paclitaxel, daunorubicin, docetaxel, cisplatin, and 5-fluorouracil.

Paeoniae radix used as an active ingredient of the composition of the present disclosure satisfies the standards of the Korean Pharmacopoeia, and is the root of *Paeonia lactiflora Pallas* which is a plant belonging to the family Paeoniaceae. It is known that Paeoniae radix has an antibacterial effect, inhibits the growth of bacteria such as *Staphylococcus aureus* and *Shigella*, and is effective against abdominal pain and diarrhea. However, the effects of Paeoniae radix on the alleviation of cachexia, such as alleviation of inappetence and inhibition of muscle loss, have not been known.

According to one embodiment of the present disclosure, the Paeoniae radix extract may be prepared according to a conventional method known in the art. For example, the Paeoniae radix extract may be prepared by pulverizing Paeoniae radix, adding thereto a solvent which is commonly used for extraction, and performing extraction at an appropriate temperature and pressure.

According to one embodiment of the present disclosure, the solvent may be selected from the group consisting of distilled water, a $C_1$ to $C_4$ lower alcohol, hexane, ethyl acetate, chloroform, diethyl ether, dichloromethane, acetone, and mixtures thereof.

Meanwhile, the Paeoniae radix extract includes not only the extract obtained by the solvent extraction method described above, but also an extract obtained through a conventional purification process. For example, the Paeoniae radix extract of the present disclosure may also include fractions obtained by additionally performing various purification processes, such as separation using an ultrafiltration membrane having a certain molecular weight cut-off value, or separation by various chromatography systems (manufactured for separation according to size, charge, hydrophobicity or affinity). In addition, the Paeoniae radix may be prepared in a powder form by additional processes such as reduced pressure distillation and freeze drying or spray drying.

According to one embodiment of the present disclosure, the Paeoniae radix extract may alleviate a symptom selected from the group consisting of inappetence, weight loss, fatigue, inflammation, muscle loss and hematopoietic toxicity, and thus may be effectively used for the alleviation, prevention or treatment of cachexia and muscle loss.

For administration, the pharmaceutical composition may be preferably formulated as a pharmaceutical composition further containing one or more pharmaceutically acceptable carriers, in addition to the Paeoniae radix extract described above.

The dosage form of the pharmaceutical composition may be granules, powders, tablets, coated tablets, capsules, suppositories, solutions, syrups, juices, suspensions, emulsions, drops, or injectable solutions. For example, for formulation in the form of tablets or capsules, the active ingredient may be combined with an oral, non-toxic pharmaceutically acceptable inert carrier such as ethanol, glycerol or water. In addition, if desired or necessary, suitable binders, lubricants, disintegrants and dyes may likewise be incorporated into the mixture. Suitable binders include, but are not limited to, starch, gelatin, natural sugars such as glucose or beta-lactose, maize sweeteners, natural and synthetic rubbers such as acacia, tragacanth gum or sodium oleate, sodium stearate, magnesium stearate, sodium benzoate, sodium acetate, sodium chloride, and the like. Disintegrants include, but are not limited to, starch, methyl cellulose, agar, bentonite, xanthan gum, and the like.

As an acceptable pharmaceutical carrier in a composition which is formulated as a liquid solution, it is possible to use one or more of saline, sterile water, Ringer's solution, buffered saline, albumin solution for injection, dextrose solution, maltodextrin solution, glycerol, ethanol, and mixtures thereof, which are suitable for sterilization and in vivo use, and other conventional additives such as antioxidants, buffers, bacteriostatic agents, etc. may be added as needed. In addition, the pharmaceutical composition may be formulated as injectable formulations such as an aqueous solution, suspension or emulsion, pills, capsules, granules or tablets by additionally adding a diluent, a dispersant, a surfactant, a binder, and a lubricant.

The pharmaceutical composition of the present disclosure may be administered orally or parenterally. For parenteral administration, the pharmaceutical composition may be administered by intravenous injection, subcutaneous injection, intramuscular injection, intraperitoneal injection, transdermal administration, or the like.

A suitable dose of the pharmaceutical composition of the present disclosure may be determined depending on factors such as the formulation method, the mode of administration, the patient's age, weight, sex, pathological condition and diet, the duration of administration, the route of administration, excretion rate, and response sensitivity. According to one embodiment of the present disclosure, the daily dose of the pharmaceutical composition of the present disclosure is 0.001 to 10 g/kg.

The pharmaceutical composition of the present disclosure may be prepared in single-dose forms or in multi-dose packages by formulation using a pharmaceutically acceptable carrier and/or excipient according to a method that may be easily carried out by those skilled in the art.

Another aspect of the present disclosure provides a food composition for preventing or alleviating cachexia and muscle loss, the food composition containing a Paeoniae radix extract as an active ingredient.

The food composition according to the present disclosure may be used as a functional food obtained by formulation in the same manner as the pharmaceutical composition, or may be added to various foods. Foods to which the composition of the present disclosure may be added include, for example, beverages, confectionery, diet bars, dairy products, meats, chocolate, pizza, ramen, other noodles, gums, ice creams, vitamin complexes, and health food supplements.

The food composition of the present disclosure may contain ingredients that are commonly added in food production, in addition to containing the Paeoniae radix extract as an active ingredient. For example, the food composition contains proteins, carbohydrates, fats, nutrients, seasoning agents and flavoring agents. Examples of the carbohydrates include conventional sugars, such as monosaccharides (e.g., glucose, fructose, etc.), disaccharides (e.g., maltose, sucrose, etc.), polysaccharides (e.g., dextrin, cyclodextrin, etc.), and sugar alcohols such as xylitol, sorbitol, erythritol or the like. Examples of flavoring agents that may be used include natural flavoring agents (thaumatin, *stevia* extracts, such as rebaudioside A, glycyrrhizin, etc.) and synthetic flavoring agents (saccharin, aspartame, etc.). For example, when the food composition of the present disclosure is prepared as a drink or a beverage, it may further contain citric acid, liquid fructose, sugar, glucose, acetic acid, malic acid, fruit juice, and various plant extracts, in addition to the Paeoniae radix extract of the preset invention.

Still another aspect of the present disclosure provides an anticancer adjuvant containing, as an active ingredient, the pharmaceutical composition for preventing or treating cachexia and muscle loss.

As used herein, the term "anticancer adjuvant" refers to an adjuvant exhibiting the effect of alleviating the side effects of an anticancer drug during anticancer treatment. The side effects of the anticancer drug include hematopoietic toxicity, inappetence, weight loss, and the like.

The anticancer adjuvant may further contain one or more active ingredients that exhibit the same or similar functions, in addition to containing the Paeoniae radix extract as an active ingredient. The anticancer adjuvant may be administered orally or parenterally during clinical administration. For parenteral administration, the anticancer adjuvant may be administered by intraperitoneal injection, intrarectal injection, subcutaneous injection, intravenous injection, intramuscular injection, intrauterine dural injection, intracerebrovascular injection, or intrathoracic injection, and may be used in the form of a general pharmaceutical formulation.

The anticancer adjuvant may be used alone or in combination with surgery, radiotherapy, hormone therapy, chemotherapy, and methods using a biological response modifier. The daily dose of the anticancer adjuvant is about 0.0001 to 1,000 mg/kg, preferably 1 to 100 mg/kg, and the anticancer adjuvant may be administered once or several times a day. However, the range of the daily dose of the anticancer adjuvant varies depending on the patients' body weight, age, sex, health condition and diet, the duration of administration, the mode of administration, excretion rate, and the severity of the disease. The anticancer adjuvant of the present disclosure may be administered in various parenteral formulations at the time of actual clinical administration. For formulation, the anticancer adjuvant is prepared with diluents or excipients which are commonly used, such as fillers, extenders, binders, wetting agents, disintegrants, surfactants, etc. Formulations for parenteral administration include sterilized aqueous solutions, non-aqueous solutions, suspensions, emulsions, freeze-dried preparations, and suppositories. As non-aqueous solvents or suspending agents, it is possible to use propylene glycol, polyethylene glycol, vegetable oils such as olive oil, injectable esters such as ethyl oleate, and the like. As a base for suppositories, it is possible to use witepsol, Macrogol, Tween 61, cacao butter, laurin fat, glycerogelatin, and the like.

Yet another aspect of the present disclosure provides a method of preventing or treating cachexia and muscle loss by administering a composition containing a Paeoniae radix extract as an active ingredient.

The composition containing a Paeoniae radix extract as an active ingredient according to the present disclosure may alleviate inappetence, weight loss, muscle loss and fatigue and inhibit hematopoietic toxicity. Thus, the composition may be effectively used for the prevention or treatment of cachexia and muscle loss

MODE FOR DISCLOSURE

Hereinafter, one or more embodiments will be described in more detail with reference to examples. However, these examples are to illustrate one or more embodiments, and the scope of the present disclosure is not limited to these examples.

Example 1. Preparation of Paeoniae Radix Extract 250 g of Paeoniae radix and 2 L of 30% ethanol were placed in a 3-L reactor, and extracted under reflux using a reflux extractor at 65° C. for 4 hours. The first extract was filtered, and 2 L of 30% ethanol was added again to the residue, followed by second extraction under the same conditions. Thereafter, the second extract was filtered and mixed with the first extract, and then the resulting extract was concentrated at 50° C. or lower to remove the ethanol. The concentrated extract was freeze-dried and then homogenized with a mixer. As a result of extract preparation, a Paeoniae radix extract having a dry weight of 43 g (17.20% yield) could be obtained.

Example 2. Alleviation Effect of Paeoniae Radix Extract on Cachexia and Muscle Loss Induced by Tumor 2-1. Preparation of Experimental Animals and Experimental Method As experimental animals, 4-week-old male C57BL/6 mice (weighed 18 to 20 g) were purchased from Central Lab Animal Inc., acclimated in a laboratory animal facility for 1 week, and then used in the experiment. During the experiment, the animals were allowed to access feed and water ad libitum, and housed at cages at a temperature of 22±2° C. and a relative humidity of 60±5% under a 12-hr light/12-hr dark cycle.

The mice were divided into a normal group (healthy group), a control group (tumor-induced group), a conventional drug-administered group and a Paeoniae radix extract-administered group, each group consisting of 9 animals. Each animal of the normal group was injected subcutaneously with 100 μl of PBS, and the tumor-induced group (control group), the conventional drug-administered group and the Paeoniae radix extract-administered group were injected subcutaneously with MC38 colorectal cancer cells ($1 \times 10^6$ cells/100 μl) or Lewis lung carcinoma (LLC) cells ($1 \times 10^6$ cells/100 μl). When the tumor volume reached about 1,000 mm$^3$ after 2 weeks of tumor induction, the cancer cachexia treatment agent Megace (megestrol acetate), which is most frequently used in current clinical practice, was administered orally to the conventional drug-administered group. Dose of Megace was 125 mg/kg (=625 mg [daily human dose]/60 kg [human's average body weight]×12 [human/mouse body surface area dose equivalent factor]) for 14 days. Paeoniae radix extract prepared in Example 1 was administered orally to the Paeoniae radix extract-administered group for 14 days at a dose of 100 mg/kg, which is slightly lower than the dose of Megace. During the experiment, the food uptake of each mouse was recorded. In addition, the muscle strength of each mouse was measured with a grip strength test device (Bioseb, USA), and the endurance of each mouse was measured under the condition of maximum exercise time of 600 seconds using a treadmill device (Columbus Instrument, USA).

After completion of the experiment, the mice were euthanized, blood was collected therefrom, and then the tumor weight and the hind limb muscle weight were measured, and the serum and muscle concentrations of TNF-α, IL-6, IL-1 and MCP-1 were quantified by ELISA assay. In addition, the effect of the Paeoniae radix extract on the reduction of muscle atrophy factor (MAFbx) in the hind limb muscle of each LCC cancer-bearing mouse was measured using Western blot and immunofluorescence known in the art.

2-2. Appetite Stimulating Effect of Paeoniae Radix Extract

Figure 1:
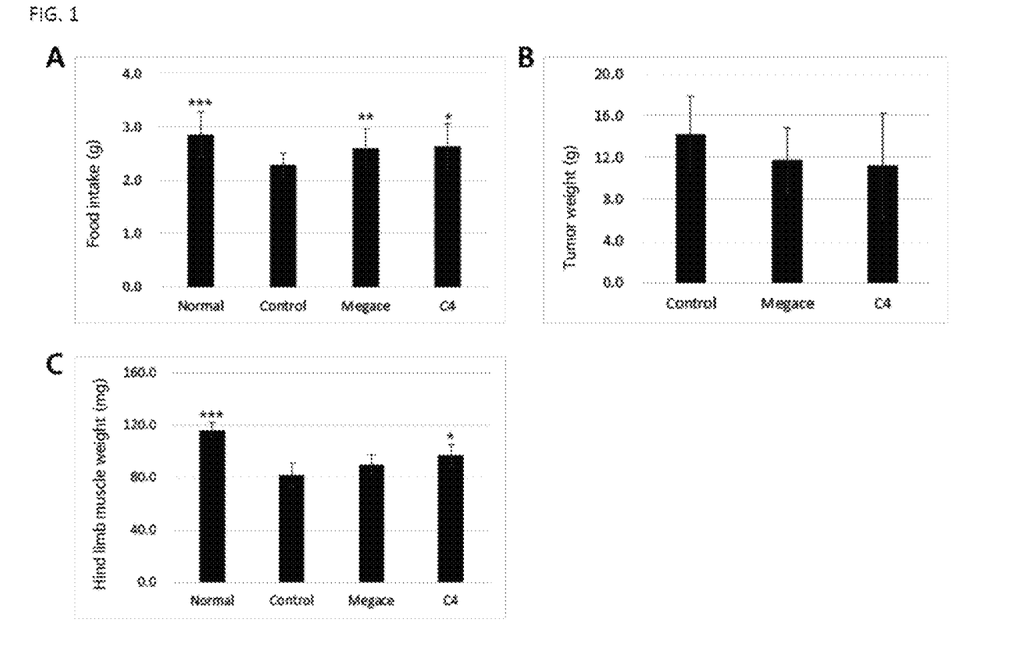
FIG. 1 shows the results of measuring food intake (A), tumor weight (B) and hind limb muscle weight (C) after administering a Paeoniae radix extract (C4) to mice with tumors induced by MC38 colorectal cancer cells.
Figure 5:
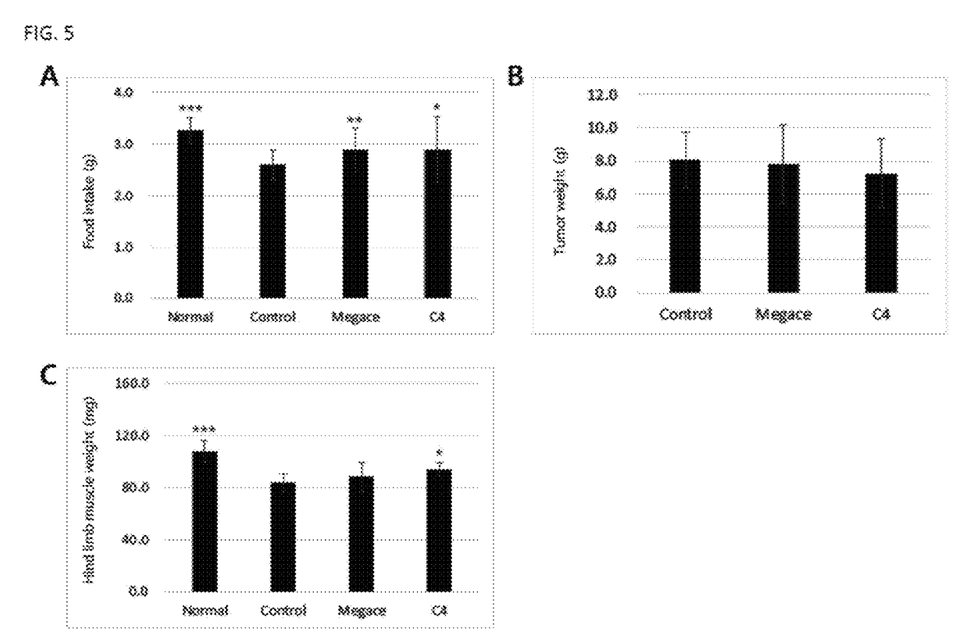
FIG. 5 shows the results of measuring food intake (A), tumor weight (B) and hind limb muscle weight (C) after administering a Paeoniae radix extract (C4) to mice with tumors induced by LLC cells.

While the Paeoniae radix extract was administered orally to the mice for 14 days after tumor induction, the food intake of the mice was recorded. As a result, as shown in Table 1 below and FIGS. 1A and 5A (shown as C4 in FIGS), it could be confirmed that the food intake increased in the Paeoniae radix extract-administered group compared to the tumor-induced group (control group). In Table 1 below, *,  and * indicate p<0.05, p<0.01 and p<0.001, respectively, and they are also used in the same meaning in the Tables described below and the Figures.

TABLE 1

| | | Food intake (g) | |
|---|---|---|---|
| | | Mean ± standard deviation | p-value: unpaired t-test compared to control group |
| MC38 | Normal group | 2.855 ± 0.417 | 0.000*** |
| | Control group (tumor-induced group) | 2.287 ± 0.220 | 1.000 |
| | Conventional drug-administered group | 2.607 ± 0.357 | 0.008** |
| | Paeoniae radix extract-administered group | 2.634 ± 0.424 | 0.011* |
| LLC | Normal group | 3.266 ± 0.247 | 0.000*** |
| | Control group (tumor-induced group) | 2.599 ± 0.283 | 1.000 |
| | Conventional drug-administered group | 2.891 ± 0.417 | 0.003** |
| | Paeoniae radix extract-administered group | 2.884 ± 0.639 | 0.029* |

Meanwhile, as can be seen in FIG. 6, in the case of the food intake (FIG. 6A) and body weight (FIG. 6B) of the LLC cancer-bearing mice to which the Paeoniae radix extract was administered at a dose of 50, 100 or 200 mg/kg, the food intake and the body weight of the group administered at a dose of 100 mg/kg were most significantly increased, indicating that the optimum dose of the Paeoniae radix extract is 100 mg/kg.

2-3. Effect of Paeoniae Radix Extract on Tumor Weight

After the Paeoniae radix extract was administered orally to the mice for 14 days after tumor induction, the mice were euthanized and the tumor weight was measured. As shown in Table 2 below and FIGS. 1B and 5B, no significant difference was found in the tumor weight of the Paeoniae radix extract-administered group compared to that of the tumor-induced group (control group).

TABLE 2

| | | Tumor weight (g) | |
|---|---|---|---|
| | | Mean ± standard deviation | p-value: unpaired t-test compared to control group |
| MC38 | Control group (tumor-induced group) | 14.239 ± 3.627 | 1.000 |
| | Conventional drug-administered group | 11.747 ± 3.073 | 0.311 |
| | Paeoniae radix extract-administered group | 11.224 ± 5.036 | 0.272 |
| LLC | Control group (tumor-induced group) | 8.083 ± 1.674 | 1.000 |
| | Conventional drug-administered group | 7.797 ± 2.385 | 0.804 |
| | Paeoniae radix extract-administered group | 7.226 ± 2.118 | 0.417 |

Figure 7:
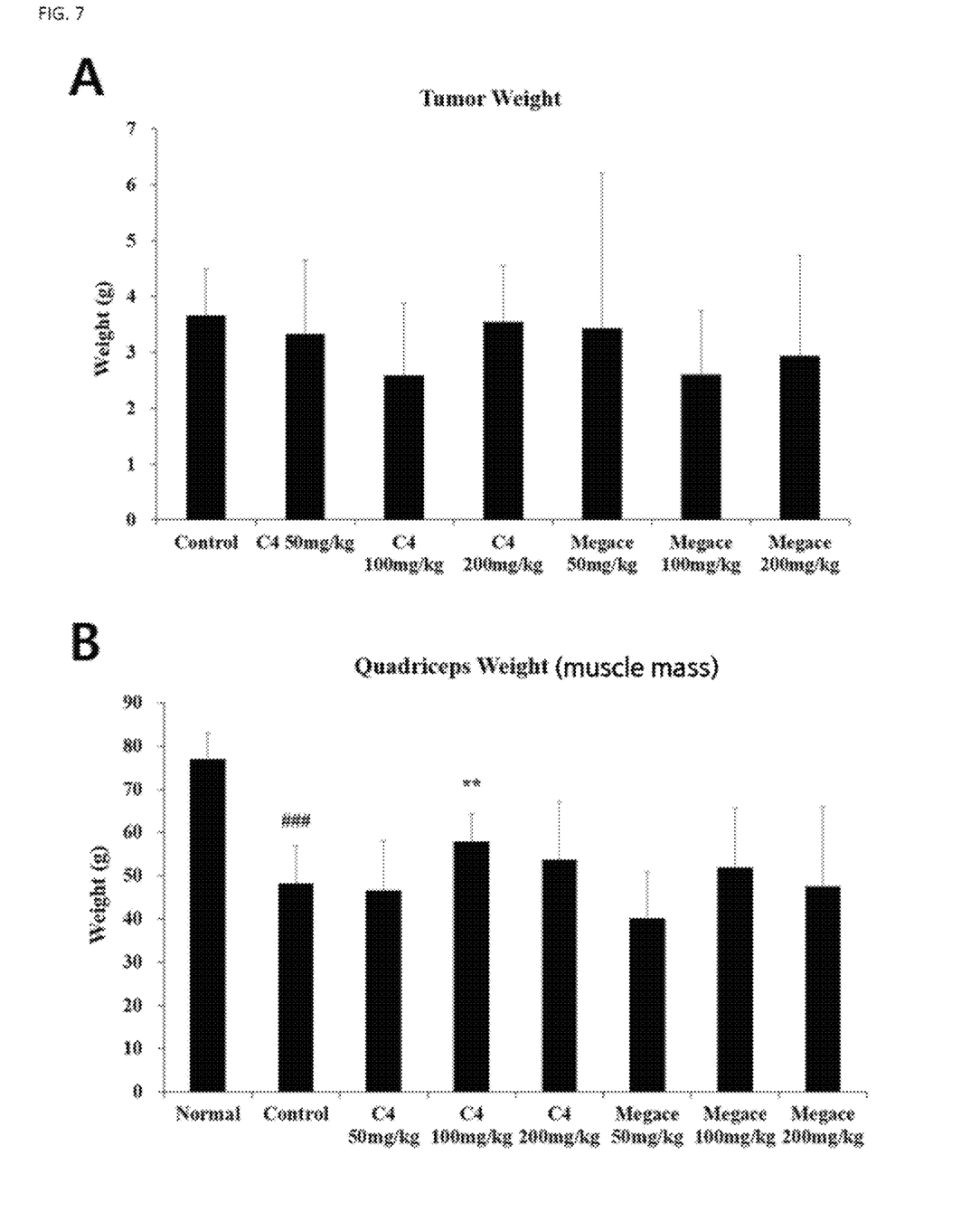
FIG. 7 shows the results of measuring tumor weight (A) and hind limb muscle weight (B) depending on dose after administering a Paeoniae radix extract at a dose of 50, 100 or 200 mg/kg to mice with tumors induced by LLC cells.

Meanwhile, as can be seen in FIG. 7A, it was confirmed that the tumor weight of the LLC cancer-bearing mice, to which the Paeoniae radix extract was administered at a dose of 50, 100 or 200 mg/kg, did not significantly differ from that of tumor-induced group (control group).

That is, it was confirmed that the effect of the Paeoniae radix extract on the alleviation of cachexia and muscle loss was not attributable to its anticancer effects.

2-4. Effect of Paeoniae Radix Extract on Muscle Weight

After the Paeoniae radix extract was administered orally to the mice for 14 days after tumor induction, the mice were euthanized and the hind limb muscle weight was measured. As a result, as shown in Table 3 below and FIGS. 1C and 5C, it was confirmed that the hind limb muscle weight significantly increased in the Paeoniae radix extract-administered group compared to the tumor-induced group (control group)

TABLE 3

| | | Hind limb muscle weight (g) | |
|---|---|---|---|
| | | Mean ± standard deviation | p-value: unpaired t-test compared to control group |
| MC38 | Normal group | 116.729 ± 5.323 | 0.000*** |
| | Control group (tumor-induced group) | 82.280 ± 8.918 | 1.000 |
| | Conventional drug-administered group | 90.438 ± 7.057 | 0.093 |
| | Paeoniae radix extract-administered group | 97.260 ± 8.505 | 0.026* |
| LLC | Normal group | 107.700 ± 8.706 | 0.000*** |
| | Control group (tumor-induced group) | 83.333 ± 6.772 | 1.000 |
| | Conventional drug-administered group | 88.000 ± 11.023 | 0.410 |
| | Paeoniae radix extract-administered group | 93.883 ± 5.307 | 0.014* |

Meanwhile, as can be seen in FIG. 7B, in the case of the hind limb muscle weight of the LLC cancer-bearing mice to which the Paeoniae radix extract was administered at a dose of 50, 100 or 200 mg/kg, the effect of increasing the hind limb muscle weight was the best in the group to which the Paeoniae radix extract was administered at a dose of 100 mg/kg, indicating that the optimum dose of the Paeoniae radix extract is 100 mg/kg.

Figure 2:
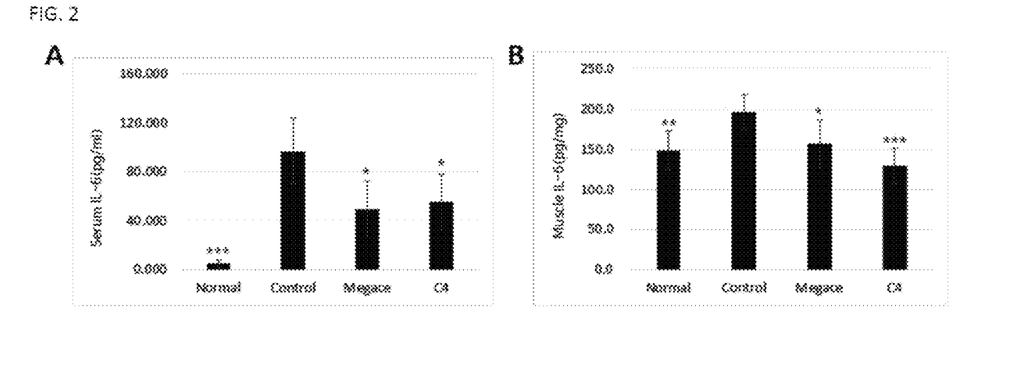
FIG. 2 shows the results of measuring serum IL-6 concentration (A) and muscle IL-6 concentration (B) after administering a Paeoniae radix extract to mice with tumors induced by MC38 colorectal cancer cells.
Figure 8:
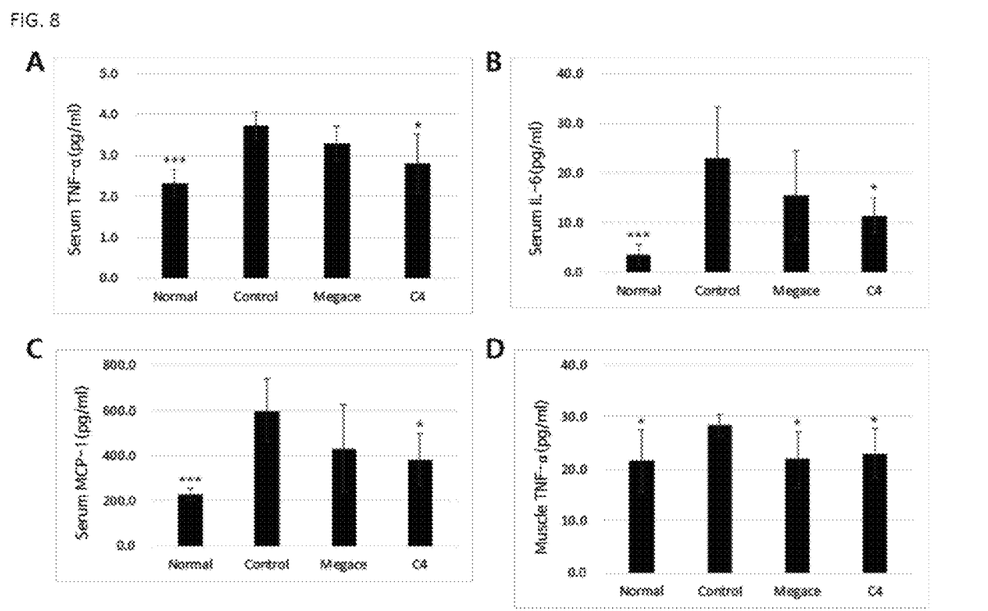
FIG. 8 shows the results of measuring the serum concentrations of TNF-α (A), IL-6 (B) and MCP-1 (C) and the muscle concentration of TNF-α (D) after administering a Paeoniae radix extract to mice with tumors induced by LLC cells.

2-5. Effect of Paeoniae Radix Extract on Prevention of Muscle Loss Based on Changes in Inflammatory Cytokine Concentration After the Paeoniae radix extract was administered orally to the mice for 14 days after tumor induction, the mice were euthanized and the serum and muscle concentrations of inflammatory cytokines were measured. As a result, as shown in Table 4 below and FIGS. 2 and 8, the concentrations of tumor-induced inflammatory cytokines increased in the control group (tumor-induced group) compared to the normal (healthy) group. It was confirmed that and that the serum and muscle concentrations of inflammatory cytokines significantly decreased in the Paeoniae radix extract-administered group compared to the control group, indicating that the Paeoniae radix extract exhibited the effect of alleviating inflammation and muscle loss.

TABLE 4

| | | | Cytokine concentration (pg/ml) | |
|---|---|---|---|---|
| | | | Mean ± standard deviation | p-value: unpaired t-test compared to control group |
| MC38 | Serum IL-6 | Normal group | 4.840 ± 3.197 | 0.000*** |
| | | Control group (tumor-induced group) | 96.667 ± 27.119 | 1.000 |
| | | Conventional drug-administered group | 49.222 ± 22.762 | 0.027* |
| | | Paeoniae radix extract-administered group | 55.175 ± 22.456 | 0.016* |
| | Muscle IL-6 | Normal group | 148.250 ± 24.813 | 0.004** |
| | | Control group (tumor-induced group) | 196.000 ± 21.069 | 1.000 |
| | | Conventional drug-administered group | 156.167 ± 29.486 | 0.049* |
| | | Paeoniae radix extract-administered group | 129.083 ± 22.249 | 0.000*** |
| LLC | Serum TNF-α | Normal group | 2.331 ± 0.318 | 0.000*** |
| | | Control group (tumor-induced group) | 3.732 ± 0.338 | 1.000 |
| | | Conventional drug-administered group | 3.302 ± 0.422 | 0.113 |
| | | Paeoniae radix extract-administered group | 2.800 ± 0.717 | 0.026* |
| | Serum IL-6 | Normal group | 3.545 ± 2.254 | 0.000*** |
| | | Control group (tumor-induced group) | 22.913 ± 10.246 | 1.000 |
| | | Conventional drug-administered group | 15.616 ± 8.902 | 0.229 |
| | | Paeoniae radix extract-administered group | 11.440 ± 3.656 | 0.025* |
| | Serum MCP-1 | Normal group | 229.498 ± 26.674 | 0.000*** |
| | | Control group (tumor-induced group) | 598.598 ± 140.930 | 1.000 |
| | | Conventional drug-administered group | 431.670 ± 191.640 | 0.282 |
| | | Paeoniae radix extract-administered group | 382.118 ± 114.198 | 0.038* |
| | Muscle TNF-α | Normal group | 21.632 ± 5.931 | 0.030* |
| | | Control group (tumor-induced group) | 28.462 ± 1.987 | 1.000 |
| | | Conventional drug-administered group | 21.910 ± 5.414 | 0.031* |
| | | Paeoniae radix extract-administered group | 23.000 ± 4.734 | 0.045* |

Figure 3:
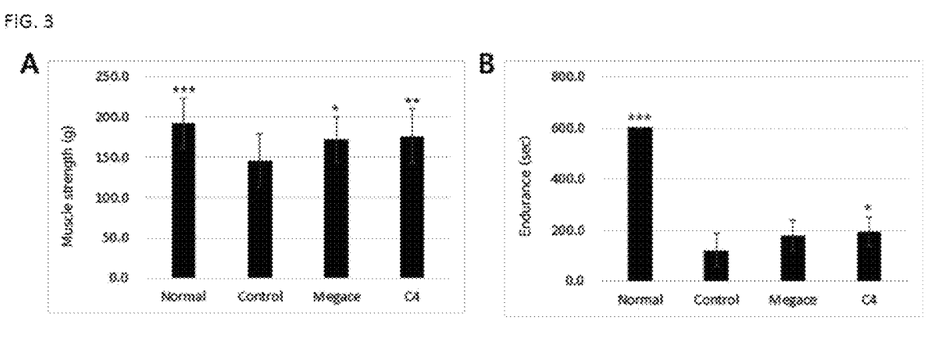
FIG. 3 shows the results of measuring muscle strength (A) and endurance (B) after administering a Paeoniae radix extract to mice with tumors induced by MC38 colorectal cancer cells.
Figure 9:
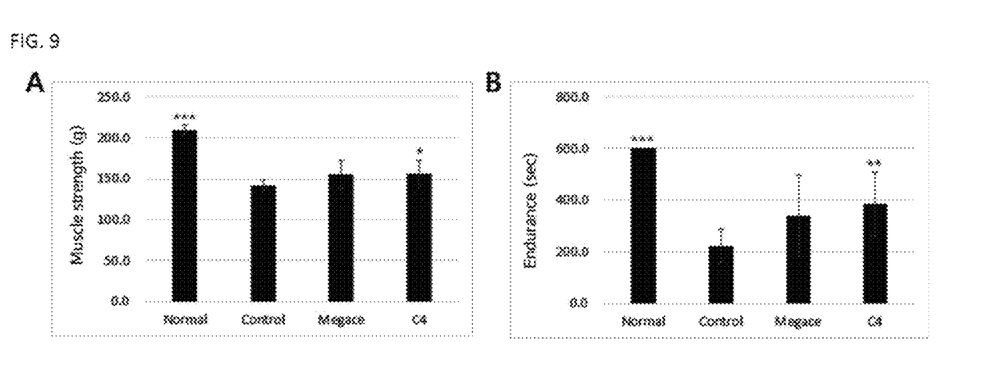
FIG. 9 shows the results of measuring muscle strength (A) and endurance (B) after administering a Paeoniae radix extract to mice with tumors induced by LLC cells.

2-6. Effect of Paeoniae Radix Extract on Improvement of Muscle Strength and Endurance On day 12th day of the oral treatment of conventional drug or the Paeoniae radix extract to the tumor-induced mice, the muscle strength and endurance of the mice were measured by a grip strength (g) test and a treadmill running time (sec) test, respectively. As a result, as shown in Tables 5 and 6 below and FIGS. 3 and 9, it was confirmed that the muscle strength and the endurance significantly decreased in the control group compared to the normal group. On the other hand, it was confirmed that the muscle strength and the endurance significantly increased in the Paeoniae radix extract-administered group compared to the control group, indicating that the Paeoniae radix extract improved the muscle strength and endurance of the tumor-bearing mice.

TABLE 5

| | | Muscle strength (g) | |
|---|---|---|---|
| | | Mean ± standard deviation | p-value: unpaired t-test compared to control group |
| MC38 | Normal group | 191.807 ± 31.236 | 0.000*** |
| | Control group (tumor-induced group) | 145.500 ± 33.357 | 1.000 |
| | Conventional drug-administered group | 172.065 ± 28.210 | 0.010* |
| | Paeoniae radix extract-administered group | 176.039 ± 33.776 | 0.008** |
| LLC | Normal group | 209.295 ± 5.535 | 0.000*** |
| | Control group (tumor-induced group) | 141.433 ± 6.712 | 1.000 |
| | Conventional drug-administered group | 154.883 ± 17.238 | 0.052 |
| | Paeoniae radix extract-administered group | 155.650 ± 16.410 | 0.032* |

TABLE 6

| | | Endurance (sec) | |
|---|---|---|---|
| | | Mean ± standard deviation | p-value: unpaired t-test compared to control group |
| MC38 | Normal group | 600.000 ± 0.000 | 0.000*** |
| | Control group (tumor-induced group) | 120.625 ± 65.687 | 1.000 |
| | Conventional drug-administered group | 177.400 ± 60.844 | 0.076 |
| | Paeoniae radix extract-administered group | 192.889 ± 58.076 | 0.029* |
| LLC | Normal group | 600.000 ± 0.000 | 0.000*** |
| | Control group (tumor-induced group) | 222.400 ± 65.243 | 1.000 |
| | Conventional drug-administered group | 338.333 ± 157.322 | 0.056 |
| | Paeoniae radix extract-administered group | 383.714 ± 124.440 | 0.003** |

Figure 10:
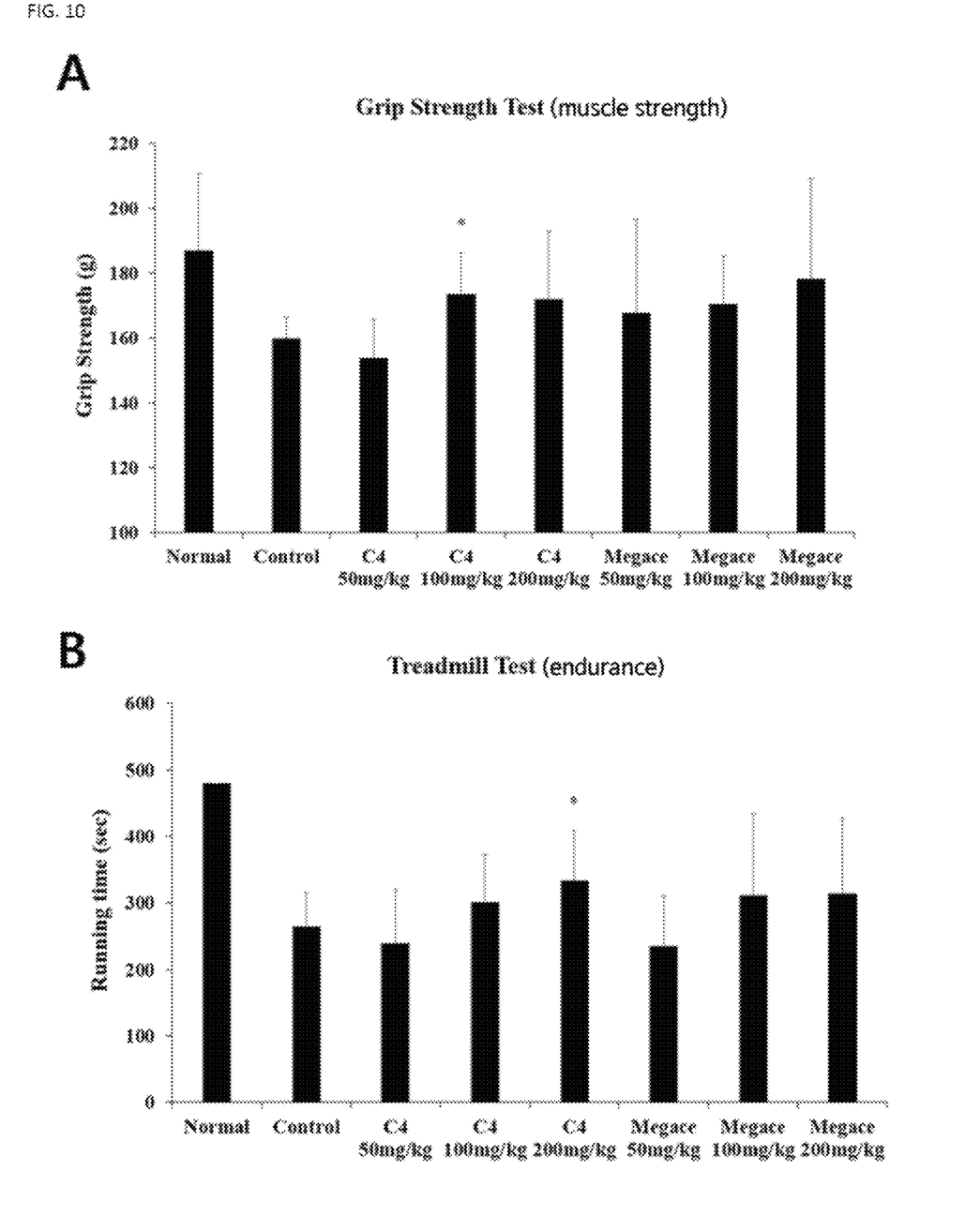
FIG. 10 shows the results of measuring muscle strength (A) and endurance (B) depending on dose after administering a Paeoniae radix extract at a dose of 50, 100 or 200 mg/kg to mice with tumors induced by Lewis lung carcinoma (LLC) cells.

Meanwhile, as can be seen in FIG. 10, in the case of the muscle strength (FIG. 10A) and endurance (FIG. 10B) of the LLC cancer-bearing mice to which the Paeoniae radix extract was administered at a dose of 50, 100 or 200 mg/kg, the effect of the increasing the muscle strength and the endurance was the best in the group to which the Paeoniae radix extract was administered at a dose of 100 mg/kg, indicating that the optimum dose of the Paeoniae radix extract is 100 mg/kg.

2-7. Effect of Paeoniae Radix Extract on Reduction of Muscle Atrophy Factor

Figure 4:
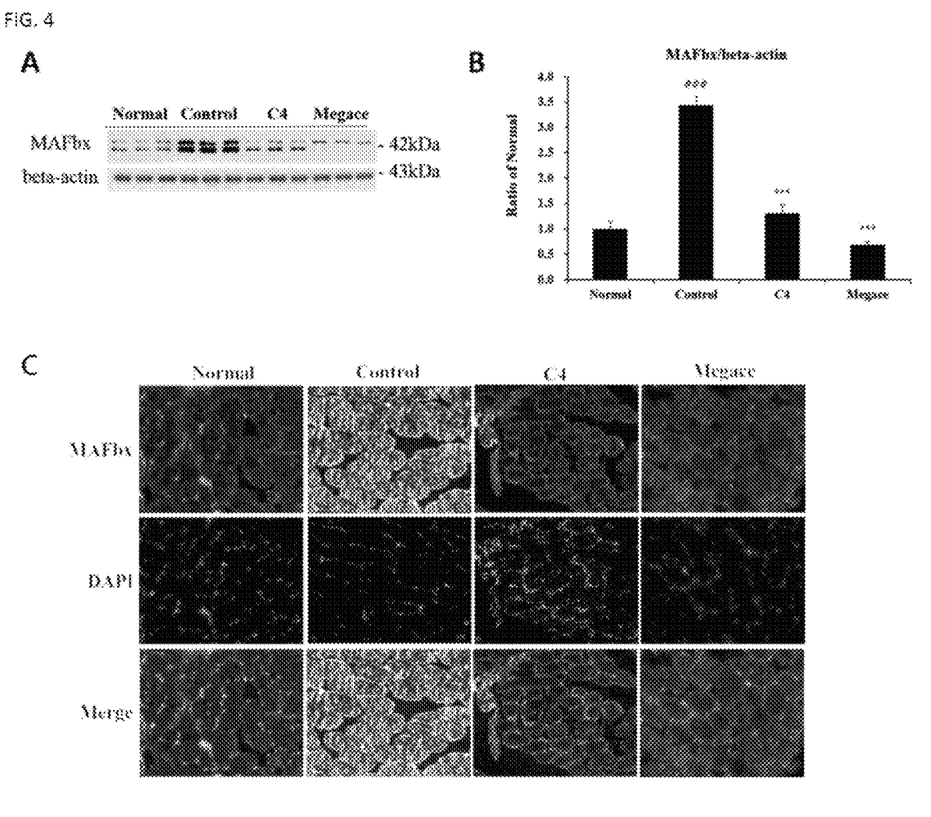
FIG. 4 shows the results of Western blot assay (A and B) and immunofluorescence assay (C) performed to measure muscle atrophy factor (MAFbx) in hind limb muscle after administering a Paeoniae radix extract to mice with tumors induced by Lewis lung carcinoma (LLC) cells.

After the Paeoniae radix extract was administered orally to the mice for 14 days after tumor induction, the mice were euthanized, and the effect of reducing the muscle atrophy factor (MAFbx) in the hind limb muscle of the LLC cancer-bearing mice was measured using Western blot and immunofluorescence known in the art. As a result, as shown in FIG. 4, it was confirmed that the muscle atrophy factor significantly increased in the control group compared to the normal group. On the other hand, the muscle atrophy factor significantly decreased in the Paeoniae radix extract-administered group compared to the control group.

Example 3. Effect of Paeoniae Radix Extract on Alleviation of Cachexia Caused by Anticancer Drug 3-1. Preparation of Experimental Animals As experimental animals, 4-week-old male C57BL/6 mice (weighed 18 to 20 g) were purchased from Central Lab Animal Inc., acclimated in a laboratory animal facility for 1 week, and then used in the experiment. During the experiment, the animals were allowed to access feed and water ad libitum, and housed in cages at a temperature of 22±2° C. and a relative humidity of 60±5% under a 12-hr light/12-hr dark cycle.

The mice were divided into a normal group, a control group and a Paeoniae radix extract-administered group, each group consisting of 9 animals. To the groups other than the normal (healthy) group, the anticancer drug 5-fluorouracil (hereinafter referred to as 5-FU), which is commonly used against cancer of the digestive system, was administered intraperitoneally once at a dose of 200 mg/kg to induce anticancer drug's side effects. Seven days after administration of 5-FU, distilled water (control group) or the Paeoniae radix extract (500 mg/kg) was administered orally to each group for 7 days, and the body weight and food intake of the mice were recorded during the experiment.

3-2. Effect of Paeoniae Radix Extract on Weight Gain and Appetite Stimulation

Figure 11:
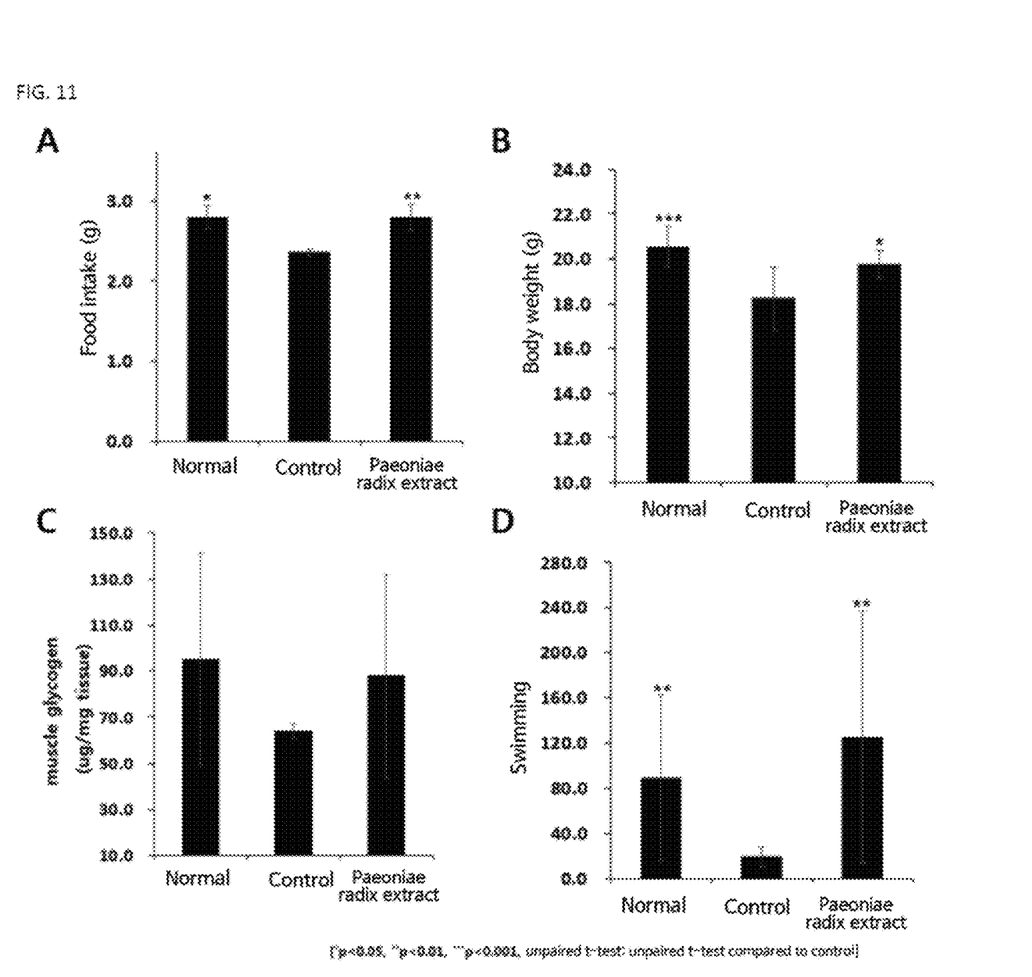
FIG. 11 shows the results of measuring food intake (A), body weight (B) and muscle glycogen concentration (C) after administering a Paeoniae radix extract to mice in which anticancer drug's side effects were induced, and the results of performing a forced swimming test (D).

While the Paeoniae radix extract (500 mg/kg) was administered orally to the mice for 7 days after administration of 5-FU, the body weight and food intake of the mice were recorded. As a result, as shown in Table 7 and FIGS. 11A and 11B, the body weight and the food intake significantly decreased in the control group compared to the normal group, but the body weight and the food intake were restored in the Paeoniae radix extract-administered group.

TABLE 7

| | Mean ± standard deviation | | | p-value: unpaired t-test compared to control | | |
|---|---|---|---|---|---|---|
| | Normal group | Control group | Paeoniae radix extract-administered group | Normal group | Control group | Paeoniae radix extract-administered group |
| Body weight (g) | 20.545 ± 0.919*** | 18.243 ± 1.394 | 19.773 ± 0.608* | 0.0007*** | 1.000 | 0.02799* |
| Food intake (g) | 2.798 ± 0.151* | 2.359 ± 0.042 | 2.791 ± 0.161** | 0.0049* | 1.000 | 0.00683** |

3-3. Effect of Paeoniae Radix Extract on Prevention of Muscle Loss Based on Increased Muscle Glycogen After completion of the experiment, the muscles were separated from the femurs of the mice, and the concentration of glycogen in the muscles was measured according to a method known in the art.

As a result, as shown in Table 8 and FIG. 11C, it could be confirmed that the concentration of glycogen significantly decreased in the control group compared to the normal group, but was restored by administration of the Paeoniae radix extract.

TABLE 8

|  | Mean ± standard deviation | | | p-value: unpaired t-test compared to control group | | |
| --- | --- | --- | --- | --- | --- | --- |
|  | Normal group | Control group | Paeoniae radix extract-administered group | Normal group | Control group | Paeoniae radix extract-administered group |
| Muscle Glycogen (μg/mg tissue) | 95.194 ± 46.169 | 64.008 ± 2.993 | 87.891 ± 44.346 | 0.227 | 1.000 | 0.3182 |

3-4. Effect of Paeoniae Radix Extract on Relief of Fatigue

On day $6^{th}$ day of the oral treatment of the Paeoniae radix extract to the mice in which anticancer drug's side effects were induced, the fatigue of the mice was measured by a forced swimming test. After loading about 5% of the body weight of each mouse, the swimming time was measured.

As a result, as shown in Table 9 below and FIG. 11D, the swimming time significantly decreased in the control group compared to the normal group, indicating that the fatigue of the control group was significant. On the other hand, the swimming time significantly increased in the Paeoniae radix extract-administered group compared to the control group, indicating that the Paeoniae radix extract relieved the fatigue of the mice in which anticancer drug's side effects were induced.

TABLE 9

|  | Mean ± standard deviation | | | p-value: unpaired t-test compared to control group | | |
| --- | --- | --- | --- | --- | --- | --- |
|  | Normal group | Control group | Paeoniae radix extract-administered group | Normal group | Control group | Paeoniae radix extract-administered group |
| Swimming time (sec) | 89.000 ± 73.980** | 19.100 ± 9.218 | 125.200 ± 111.824** | 0.0083** | 1.000 | 0.00784** |

2-4. Effect of Paeoniae Radix Extract on Improvement of Hematopoietic Function

Figure 12:
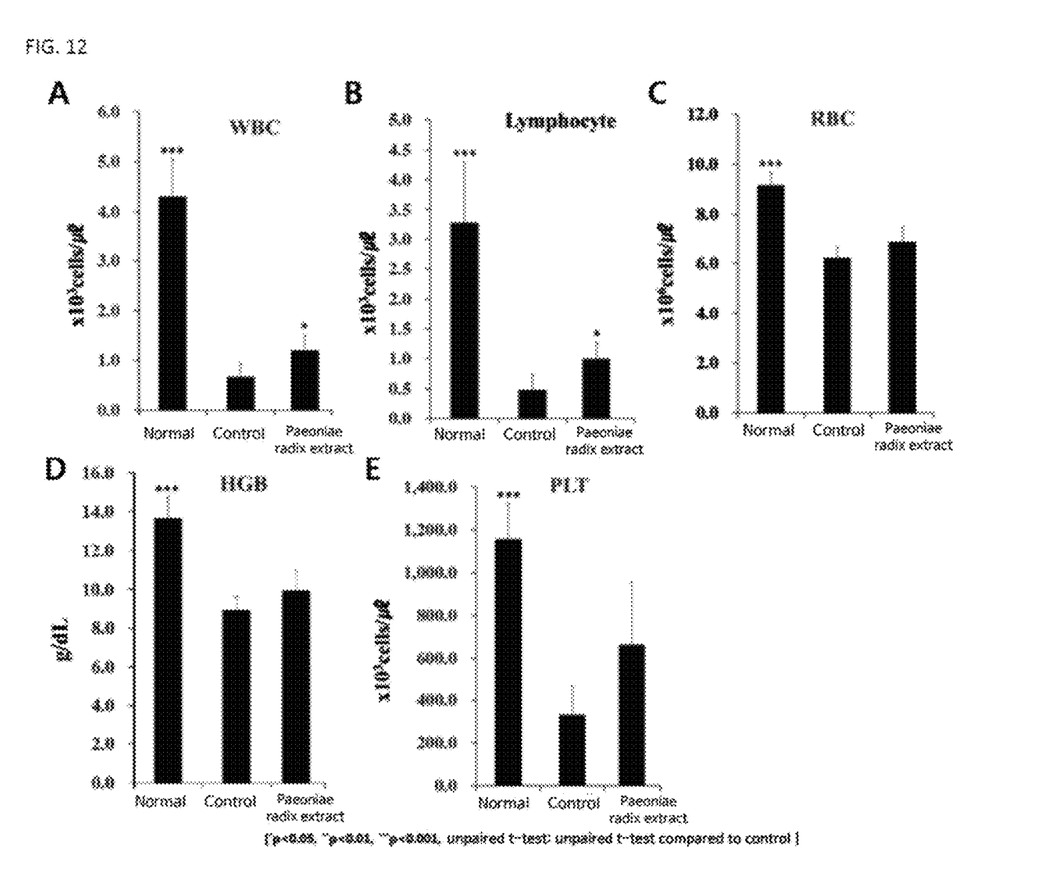
FIG. 12 shows the results of analyzing blood cells after administering a Paeoniae radix extract to mice in which anticancer drug's side effects were induced.

After the Paeoniae radix extract was administered orally to the mice for 7 days, blood was collected from the mice and analyzed with a hemocytometer. As a result, as shown in Table 10 below and FIG. 12, it could be confirmed that the number of white blood cells (WBC) and lymphocytes significantly increased in the Paeoniae radix extract-administered group compared to the control group. In addition, it could be seen that the number of platelets and red blood cells and the hemoglobin level increased in the Paeoniae radix extract-administered group compared to the control group.

TABLE 10

| Component | Normal group | Control group | Paeoniae radix extract-administered group | p-value: unpaired t-test compared to control group | | |
| --- | --- | --- | --- | --- | --- | --- |
|  |  |  |  | Normal group | Control group | Paeoniae radix extract-administered group |
| White blood cells ($\times 10^3$ cells/μl) | 4.292 ± 0.761*** | 0.674 ± 0.267 | 1.192 ± 0.312* | 0.0000*** | 1.000 | 0.0227* |
| Lymphocytes ($\times 10^3$ cells/μl) | 3.284 ± 1.009*** | 0.476 ± 0.263 | 1.000 ± 0.269* | 0.0003*** | 1.000 | 0.0144* |

TABLE 10-continued

| Component | Normal group | Control group | Paeoniae radix extract-administered group | p-value: unpaired t-test compared to control group | | |
|---|---|---|---|---|---|---|
| | | | | Normal group | Control group | Paeoniae radix extract-administered group |
| Red blood cells (x$10^6$ cells/μl) | 9.166 ± 0.513*** | 6.238 ± 0.394 | 6.862 ± 0.622 | 0.0000*** | 1.000 | 0.095 |
| Hemoglobin (g/dL) | 13.660 ± 1.071*** | 8.940 ± 0.684 | 9.940 ± 1.035 | 0.0000*** | 1.000 | 0.1093 |
| Platelets (x$10^3$ cells/μl) | 1156.200 ± 168.637*** | 332.200 ± 136.867 | 662.800 ± 293.205 | 0.0000*** | 1.000 | 0.0517 |

The present disclosure has been described with reference to the preferred embodiments thereof. Those of ordinary skill in the art to which the present disclosure pertains can understand that the present disclosure may be embodied in modified forms without departing from the essential characteristics of the present disclosure. Therefore, the disclosed embodiments should be considered from an illustrative point of view rather than a restrictive point of view. The scope of the present disclosure is defined by the appended claims rather than the above description, and all differences within the scope equivalent thereto should be construed as being included in the present disclosure.

What is claimed is:

1. A method for alleviating and treating muscle loss and weight loss in a subject in need thereof, the method comprising
administering to the subject an effective amount of a composition comprising an active ingredient that alleviates and treats muscle loss and weight loss, wherein the active ingredient that alleviates and treats muscle loss and weight loss consists of Paeoniae radix extract,
wherein administering the effective amount of the composition to the subject prevents, alleviates and treats muscle loss and weight loss in the subject relative to a subject that has not been administered the composition.

2. The method according to claim 1, wherein the Paeoniae radix extract is obtained by extraction with a solvent selected from the group consisting of distilled water, a $C_1$ to $C_4$ lower alcohol, hexane, ethyl acetate, chloroform, diethyl ether, dichloromethane, acetone, and mixtures thereof.

3. The method of claim 1, wherein the composition is a food composition.

4. The method of claim 3, wherein the food composition comprises protein, carbohydrates, and fat.

5. The method of claim 1, wherein the composition is a pharmaceutical composition comprising the active ingredient that alleviates and treats muscle loss and weight loss, and a pharmaceutically acceptable carrier.

6. A method for alleviating and treating muscle loss and weight loss in a subject in need thereof, the method comprising administering to the subject an effective amount of a food composition comprising Paeoniae radix extract, wherein the food composition alleviates and treats muscle loss and weight loss in the subject, wherein the food composition comprises protein, carbohydrates, and fat, and wherein the administering to the subject the effective amount of the food composition alleviates and treats muscle loss and weight loss in the subject relative to a subject that has not been administered the food composition.

* * * * *